United States Patent [19]

Stoddart

[11] Patent Number: 4,725,147

[45] Date of Patent: Feb. 16, 1988

[54] CALIBRATION METHOD AND APPARATUS FOR OPTICAL-RESPONSE TISSUE-EXAMINATION INSTRUMENT

[75] Inventor: Hugh F. Stoddart, Groton, Mass.

[73] Assignee: Somanetics Corporation, Troy, Mich.

[21] Appl. No.: 651,575

[22] Filed: Sep. 17, 1984

[51] Int. Cl.$^4$ ............................................. G01N 21/01
[52] U.S. Cl. ...................................... 356/433; 356/243
[58] Field of Search ........ 356/243, 236, 448, 432–433, 356/408, 246, 446; 250/252.1; 128/633, 665

[56] References Cited

U.S. PATENT DOCUMENTS

| | | | |
|---|---|---|---|
| 3,874,799 | 4/1975 | Isaacs et al. | 356/236 X |
| 4,223,995 | 9/1980 | Fletcher | 356/243 X |
| 4,467,812 | 8/1984 | Stoller | 128/665 X |
| 4,566,798 | 1/1986 | Haas | 356/243 X |
| 4,570,638 | 2/1986 | Stoddart et al. | 356/665 |

*Primary Examiner*—R. A. Rosenberger
*Attorney, Agent, or Firm*—Price, Heneveld, Cooper, DeWitt & Litton

[57] ABSTRACT

The specification discloses apparatus and methodology for calibrating optical-response tissue-examination apparatus of the type having an optical probe with at least one light-sending terminal portion adapted for introducing light into a test subject and a terminal portion for receiving resulting light from such subject. The calibration apparatus includes a body having outer walls which enclose an internal area and define an inlet aperture and an outlet aperture adapted to receive the terminal portions of the optical probe in a manner to substantially preclude entry or exit of ambient light. Means are included within said body for conveying inlet light from the test probe along a tortuous path communicating with the outlet aperture. In a preferred embodiment, the body includes means defining an outlet aperture located near the inlet aperture, and another outlet aperture may also be provided generally opposite from the inlet aperture or at a similar position of substantially greater distance from the inlet than the first outlet aperture. Also, in a preferred embodiment, internal chambers are provided within the body, certain of which is or adapted to admit a removable sample of selected media, e.g., substances selected as analogs to the anticipated examination tissue, for example, water and/or fused quartz or carbon tetrachloride.

21 Claims, 9 Drawing Figures

CALIBRATION METHOD AND APPARATUS FOR OPTICAL-RESPONSE TISSUE-EXAMINATION INSTRUMENT

TECHNICAL AREA

This invention relates broadly to equipment and methodologies which are based upon or which utilize light as an energy form to obtain condition-indicative response data for evaluation or analysis purposes. Somewhat more particularly, the invention relates to calibration methods and apparatus for use in or with optical response methods and apparatus in tissue examination and analysis; in particular, human tissue, examined in situ and in vivo. More particularly still, the invention relates to methods and apparatus for calibrating the performance of optical probes utilized in such examination procedures, which are generally of a type having light-sending portions and light-receiving portions which cooperate together to inject light energy of a selected character into a selected tissue area and to detect or collect the light energy emerging from one or more selected positions on the tissue specimen or body.

BACKGROUND OF THE INVENTION

The utilization of light energy and the principles of physics involved therewith for purposes of examination and analysis of living tissue, in particular human tissue, is rapidly becoming recognized as a highly promising and useful methodology. One particularly advantageous such modality is described in my earlier, co-pending application Ser. No. 542,022, now U.S. Pat. No. 4,570,638, in which preferred embodiments and concepts are disclosed for carrying out such optical (i.e., light-physics) procedures, in the in vivo examination of human anatomy, in particular diagnostic breast examination. Reference is made to such co-pending application for a more complete discussion and disclosure of the apparatus and methodologies involved (such application being incorporated herein by reference).

One aspect or attribute of the methods and apparatus disclosed in the above-mentioned co-pending application comprises a manually-operated optical instrument by which light-response data is obtained from the living human tissue being examined. That instrument, which may be referred to as a "probe" (although not in a limiting sense), comprises basically a pair (or more) of probe terminals or active operating portions which are movable relative to one another for use in examination procedures by placing the selected portion of the body between the two such terminal or operative portions and bringing the latter close enough together to gently bear against opposite sides of the examination area. At least one of the terminal portions has a light-emitting member or element, for example, the end of a fiber optic bundle or cable, and at least one other such probe terminal includes at least one light-receiving sensor, detector, or other "receptor". In general, the instrument operates by pulsing light energy from the emitting element and detecting such energy, after dispersion, "scatter", and other such effects within the tissue under examination, at the sensor or collector located in the other part of the probe. While it will be understood that the actual nature of the two (or more) probe terminal portions is considerably more comprehensive than the apparatus just described, including for example, other light-sensors or collectors located at other positions as well as other possible light sources and/or positions, the basic nature of the apparatus is generally as just described.

In the use of such optical response instrumentation, it is inherently of the greatest importance that the response data which it produces be and remain consistent and comparable, and remain so throughout the useful life of the instrument in generating data for evaluation. That is, the sending and receiving characteristics of the light source and light receptors used in any two given different instruments may and probably will be at least somewhat different, and will probably change with time and usage as well. The same is true with respect to the electronic components generally, used in the data-conditioning and processing circuits, etc. Thus, if reliable data is to be obtained, and if that data is to be meaningfully compared with other data taken at different points in time and/or by different instruments, it is essential to provide a way in which correlation may be assured for all such data, e.g., a way in which calibration of the sending and receiving characteristics of all such instruments may be reliably determined and maintained.

SUMMARY OF THE INVENTION

The present invention provides methods and apparatus for achieving the above-described calibration of the light-emitting or light-injecting portions of optical probe terminals with respect to the light-collecting receptor portions of such probe terminals, for optical instrumentation of the general type discussed above.

In a first sense, the present invention provides calibration or test apparatus for insertion between two opposing optical terminals of the same test instrument, with the two such terminals being moved toward one another and seated in the opposite ends of the calibration apparatus.

The invention also provides calibration or correlation methodology by which a sequence of light-emission and light-reception steps are conducted after the aforementioned apparatus has been so positioned, by which the results obtained are in effect compared to previously-determined standards, and variations are rapidly perceived and compensated or corrected.

In a somewhat more particular sense, the apparatus provided by the invention comprises wideband attenuation and diffusion means, including a succession of sequentiallydisposed diffusion chambers interconnected by particularlydisposed apertures for passage of proportioned amounts of light energy along a labyrinthine path extending between the two probe terminals.

In a further sense, the apparatus of the invention includes a calibration device generally of the aforementioned character but having one or more sample cells disposed within the device and along the optical path therewithin, by which selected tissue samples may be examined by the selectively dispersed and attenuated light passed through the device, and/or such light may be subjected to one or more known media constituting test standards.

Further still, the calibration device preferably has means for removably receiving a standard type of sample cell, whereby different such cells may be used at different times in the same calibration device, one cell being removed and another being substituted for it, with the calibration device itself remaining in place at all times for testing.

In a physical sense, the calibration apparatus in accordance herewith is preferably structured in the form of a modular device, with removable and interchangeable components, for additionally facilitating flexibility in calibration procedures.

In addition to the above, the invention provides novel methodology for calibration optical test apparatus and correlating optical test information (data) obtained by use of such apparatus, pursuant to which the data obtained from any and all test instruments used at any and all times is made to be directly compatible and comparable, for accurate and meaningful interpretation and for obtaining meaningful data bases and compilations, and for analysis, greatly augmenting the usefulness of all such data and extending the knowledge obtainable therefrom.

The foregoing major attributes of the present invention will be seen more comprehensively, and in more detail, by consideration of the ensuing specification and the appended drawings, setting forth particular preferred embodiments of the underlying invention.

DESCRIPTION OF PREFERRED EMBODIMENTS

Figure 1:
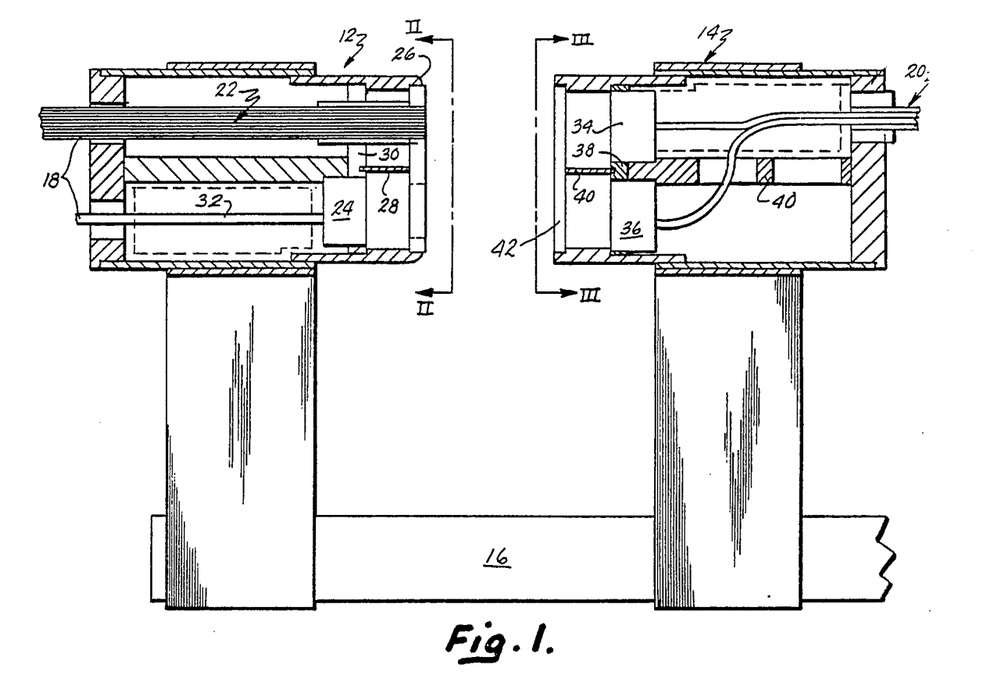
FIG. 1 is a side elevational view of an exemplary optical probe or instrument in connection with which the invention is described.

Referring first to FIG. 1, the optical response instrument depicted there for purposes of illustration comprises basically a pair of cooperative component members 12 and 14 (which may be referred to variously as "probe terminals", "component heads", etc.) which are mounted upon an interconnecting guide member 16, along which at least one of the heads or terminal members is slidably adjustable while remaining at all times in a consistent orientation with respect to the other such component or head. The guide or support 16 may incorporate length-measurement indicia or read-out means, so that the relative distance between the two component members 12 and 14 may readily be determined at any given position of adjustment since, as disclosed in the aforementioned co-pending application, the particular separation distance between the two component members 12 and 14 is very important in each different test or examination situation as an indication of optical path length, and this distance will of course vary from one patient or subject to another. Each of the two component members 12 and 14 is coupled by respective cables 18 and 20 back to a source (not shown) of required optical and/or electrical energy, as well as to various information-storage and processing means, all as disclosed in the aforementioned co-pending application. As there disclosed, the two connecting cables 18 and 20 may include either or both optical and electrical conductors, e.g., fiber optic bundles and/or current-carrying wires.

More particularly, each of the component members 12 and 14 include light-emitting and/or light-detecting elements which, depending upon the particular details of the preferred embodiment involved, may constitute electrically-operated elements or optical components, e.g., fiber-optic bundles. That is, the actual light energy to be injected may be conducted to the component head through a fiber-optic bundle and injected into the tissue under examination from the end of the fiber-optic bundle itself; conversely, light detection may be accomplished by use of an electrically-responsive light detector (e.g., a silicon photo-voltaic cell, silicon photo-diode, lead-sulfide cell, etc.) The point is, such a detector may be located either at the optical probe heads or terminals or at the opposite end of their connecting cables, within an equipment console, cabinet or the like. In the latter event, the component heads or members 12 and 14 will nonetheless emit and detect light energy, but will include only fiber-optic cable ends, as opposed to electrically-operated detectors such as photodiodes and the like.

Figure 2:
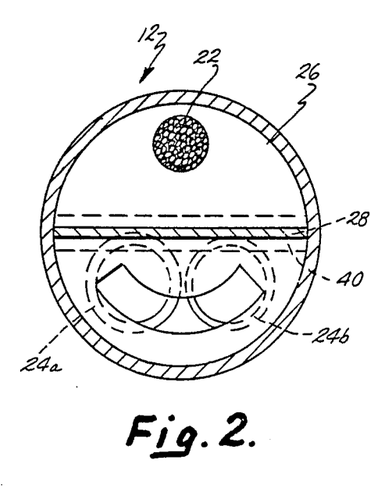
FIG. 2 is an end elevation of part of the structure shown in FIG. 1, as seen from along the plane II—II thereof and viewed in the direction of the arrows.
Figure 3:
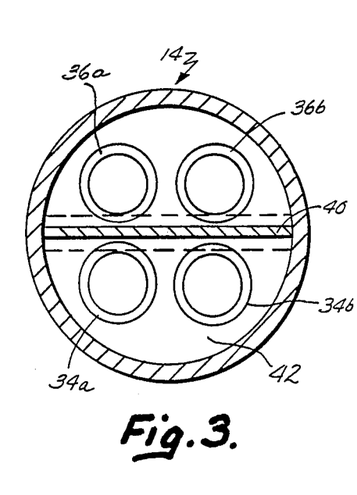
FIG. 3 is an end elevation of another part of the structure shown in FIG. 1, as seen from along the plane III—III thereof and viewed in the direction of the arrows.

Examples of typical structural configurations and relationships for the probe terminals or component members, 12 and 14 are shown in FIGS. 1, 2, and 3. Referring particularly to these figures, probe terminal 12 is depicted as including a source of light energy, in this example the end of a fiber-optic bundle 22, as well as light detection means, in the illustrated example comprising a pair of photo-voltaic cells 24a and 24b. Both he fiber-optic bundle 22 and the two photo-voltaic cells are provided access to the area immediately beyond the probe terminal (e.g., the specimen or subject from whom data is to be obtained) through an aperture plate 26 serving to otherwise close the operative end of the probe terminal. Immediately behind the aperture plate 26, a perpendicularly-positioned septum 28 extending between the rearward surface of the aperture and the front surface of a structural wall 30 in which the photo-voltaic detectors 24a and 24b are mounted serves to isolate the fiber-optic bundle from the detectors. Both the fiber-optic bundle 22 and suitable electrical connecting wire 32 from the optical detectors emerge from the probe terminal 12 and together constitute the coupling cable 18 noted above.

The probe terminal 14 is, in general, similar to probe terminal 12 described just above, except that in the embodiment illustrated this probe terminal houses only optical detectors rather than light sources (although as stated above various such arrangements, provided for purposes not integrally related to the present invention, may be encountered and are within the scope of the present invention). In the illustrated embodiment of probe terminal 14, the four detectors 34a, 34b and 36a, 36b are mounted in a structural wall or detector deck 38 analogous to the structural wall 30 noted above in connection with probe terminal 12, discussed above, and like the photo-voltaic cells 24a and 24b are recessed somewhat inwardly of the end extremity of the probe terminal. As in the case of probe terminal 12, probe terminal 14 also preferably includes a septum 40 which isolates the two detector sets (i.e., set 34a and 34b, and set 36a and 36b) from one another. The end extremity of probe terminal 14 may be closed by a desired aperture plate or filter disc 42, although this is not strictly necessary where the probe terminal includes only light-detector elements rather than a mixture of light-emission and light-detection elements.

Figure 4:
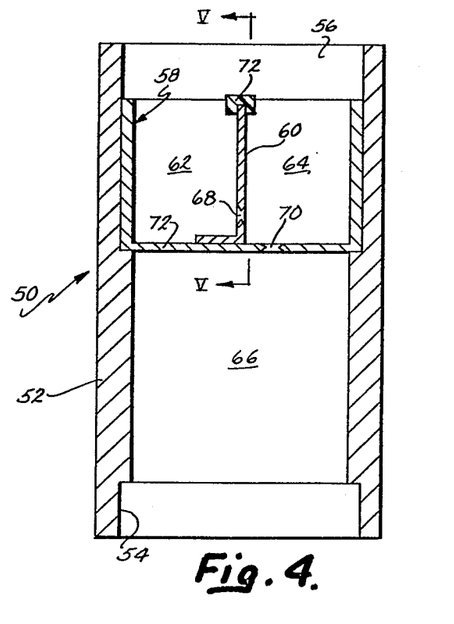
FIG. 4 is an enlarged, sectional side-elevational view of a first form of calibration instrument provided herewith.
Figure 5:
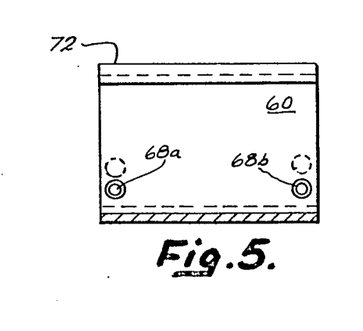
FIG. 5 is a fragmentary sectional elevational view taken along the plane V—V of FIG. 4.

A first embodiment of a test instrument calibration apparatus in accordance with the invention is illustrated in FIGS. 4 and 5. As seen there, the calibration apparatus 50 includes a generally tubular body 52 having a shape and internal diameter at each opposite end sized to receive the forward ends of probe terminals 12 and 14. Preferably, the open ends of the tubular body 52 are annularly relieved, as at 54, to the extent required to enable insertion of the endmost extremity of the probe terminals, thus substantially precluding the escape of light from between the inside of the terminal body and the outside environment, past the inserted end of the probe terminal. In the embodiment illustrated in FIGS. 4 and 5, and with reference to the probe terminal embodiments discussed above, the annular relief 54 is sized to receive the forwardmost end extremity of probe terminal 14, whereas the opposite end 56 of the tubular body 52 is intended to receive the forwardmost end of probe terminal 12.

More particularly, in the embodiment illustrated in FIG. 5, the end 56 is deeply recessed, or counterbored, to receive a cup-like insert member 58, which preferably telescopes into the tubular body 52 sufficiently to provide the aforementioned recessed are 56, which is to receive the end extremity of the probe terminal 12. Preferably, the axial extent (depth) of recess 56 should be on the same order of magnitude as that of recess 54, at the opposite end of the tubular housing. Insert cup 58 should fit snugly against the recessed side walls of the tubular housing 52, so as to block the passage of light therebetween.

Extending diametrically across the insert cup 58 is a septum member 60 which divides the cup into a first and second diffusion chamber 62 and 64, respectively. Beyond the insert cup 58, the remainder of the interior of tubular body 52 defines a further diffusion chamber 66. Diffusion chamber 62 communicates optically with diffusion chamber 64 through a pair of spaced apertures 68a and 68b extending through the bottom extremity of the septum 60. In an analogous manner, diffusion chamber 64 communicates with chamber 66 through an interconnecting aperture 70; however, in this instance there is but one aperture 70 and it is located between (essentially midway) the two septum apertures 68a and 68b. As illustrated, the septum apertures are preferably located near the bottom of the septum, i.e., near the innermost end or wall 72 of the insert cup 58, through which aperture 70 extends. As will be noted, aperture 70 is located close to, but off, the axial centerline of the tubular body 52, on which the septum 60 is aligned.

As indicated above, the calibration apparatus 50 may be considered as comprising a sequence of diffusion chambers communicating with one another and extending between the light source and the light receivers or collectors of the optical probe or test instrument. In this respect, the active ends of the probe terminals 12 and 14 are, as noted above, effectively sealed from ambient light by their close-fitting insertion into the opposite ends of the tubular housing 52 and, in the embodiment under discussion, a seal 72, of soft, black sponge-rubber or the like, is preferably provided atop the septum 60. As explained more fully below, the desired arrangement is for the septum 24 in optical probe terminal 12 to be in coplanar alignment with septum 60 such that one in effect constitutes an extension of the other, and the light source is effectively isolated from all parts of the tubular body 52 except for the first diffusion chamber 62 thereof. It is important to note that all insides surfaces of the diffusion chambers 62, 64 and 66 should be randomly textured, as by sandblasting, to produce a highly-diffusion surface; furthermore, this surface should preferably be flashed (plated or otherwise covered) with a thin layer of gold, or an optical equivalent, for minimum absorption and optimum diffusion qualitites.

For the many reasons described and discussed in the above-mentioned and incorporated co-pending application Ser. No. 542,022, in at least certain technologies and methodologies which may be carried out by use of optical test instruments such as that depicted generally by the numeral 10 in the drawings and discussed above, it is highly desirable to utilize a "near" light receiver or detector located in or reasonably close to the same probe terminal as that in which the light source is located. This near receiver corresponds to the photo-voltaic cells 24a and 24b noted above, which are thus positioned in alignment with the second diffusion chamber 64 when the correlation chamber 50 and the two probe terminals 12 and 14 are in their desired positions of relative alignment, i.e., with the septum 24 of probe terminal 12 in coplanar alignment with the septum 60 of the calibration chamber, in which position the end extremity of the fiber optic bundle 42 is aligned with the first diffusion chamber 62. Further, in the desired positioning relationship between probe terminal 14 and end 54 of the calibration chamber, septum 54' should also be aligned in a coplanar fashion with septum 60 of the correlation apparatus and septum 54 of probe terminal 12. In this relationship, each of the sets of detectors 34a, 34b and 36a, 36b will be aligned with opposite ones of the first and second diffusion chambers 62 and 64, in which position one such set of detectors will be in essentially direct alignment with the aperture 70, in the bottom of chamber 64, which as stated above is nearly axial with calibration chamber. In order to help insure proper relative positioning, an appropriate indicator mark on the outside of each of the two probe terminals and of the tubular body 52 of the calibration device may be helpful, e.g., embossed or printed arrow markers, pointers, or the like, which are to be moved into positions of mutual alignment by rotation of the calibration device into its proper position between the two probe terminals.

The use of the calibration, or correlation, apparatus 60 is described below following disclosure of a second (and preferred) embodiment in the immediately-ensuing paragraphs. It is to be noted here, however, that although the embodiment of the device 60 is described above as containing an open air-filled interior, the various "diffusion chambers" are not necessarily restricted to that media (i.e., air). On the contrary, any of such chambers may in fact contain other media, for example water, carbon tetrachloride, fused quartz, etc., depending upon the particular nature of the calibration/correlation process which is required, as dictated by the particular use being made of the optical probe instrument. With respect to such usage of non-air media in the chambers any of the latter may simply be permanently filled with the desired media and sealed; alternatively, the chambers may be configured to receive a given type of sample cell containing the desired media, or specially-shaped sample cells may be made to fit the confines of chambers such as those shown in the embodiment illustrated herein. Such cells may be made to be removable and interchangeable, so that different types of media may be used in successive, interrelated calibration sequences. Generally, it will be desired to place such media-filled sample cell in at least the first chamber 62, so that the injected light encounters (passes through) the media before encountering other chambers or outlet apertures. Additional media may also be located in other chambers, however.

FIGS. 6-9, inclusive, illustrate a second and most preferred embodiment of calibration apparatus in accordance with the invention. In this embodiment, the overall calibration apparatus is designated generally by the numeral 100 (FIG. 6) and preferably comprises three different modules 102, 104, and 106, which are made so as to interfit with one another but are preferably secured together in a manner permitting separation from one another, as by the retention set-screws designated 108 and 110. Desired mutual alignment of the modules is established and maintained by a guide pin 112 permanently mounted in the center module 104 to project in opposite directions from the ends thereof and engage in appropriate recesses in the ends of modules 102 and 106.

Module 102 may be referred to as an injector coupling module, and is analogous in some ways to the upper portion of the calibration apparatus 50 discussed above. More particularly, the injector coupling module 102 defines an open, generally cylindrical recess portion 114, which may be disposed at an angle, as shown, with respect to the longitudinal axis of the overall apparatus to accommodate optical response instruments whose heads are angled in a complementary manner to facilitate usage. The inner boundary of recess 114 is an apertured reflector plate 116, whose aperture arrangement is illustrated in FIG. 7 and includes (in the example under discussion) four equally-spaced apertures 118, 119, 120 and 121. The arrangement and sizing of these apertures should be such as to accommodate the location and size of the light sources and receptors in the particular probe terminal with which the injector module 102 is designed to mate. Thus, while the calibration device 50 described above was configured for use with the particular form of probe terminal 12 illustrated in FIGS. 1 and 2, which has a single fiber-optic bundle 22 as the light-injection source, the injector coupling 102 is designed to be used with a similar but somewhat different form of probe terminal (more particularly described in co-pending application Ser. No. 827,526, filed Feb. 10, 1986), which has a pair of oppositely-disposed and mutually-spaced fiber-optic bundles or other light emission means constituting duplicate light-injection sources, each such cable ending (or other source) being aligned with one of the openings 119, 121 in the reflector plate 116. The "near" detectors in the alternate form of probe terminal under discussion are positioned for alignment with the openings 118, 120 in the reflecting plate, being equally-spaced along an axis (probe diameter) which is perpendicular to that along which the light-injection sources are positioned. Thus, the apertures 118, 119, 120 and 121 in the reflector plate 116 are in effect arranged in quadrature.

Figure 6:
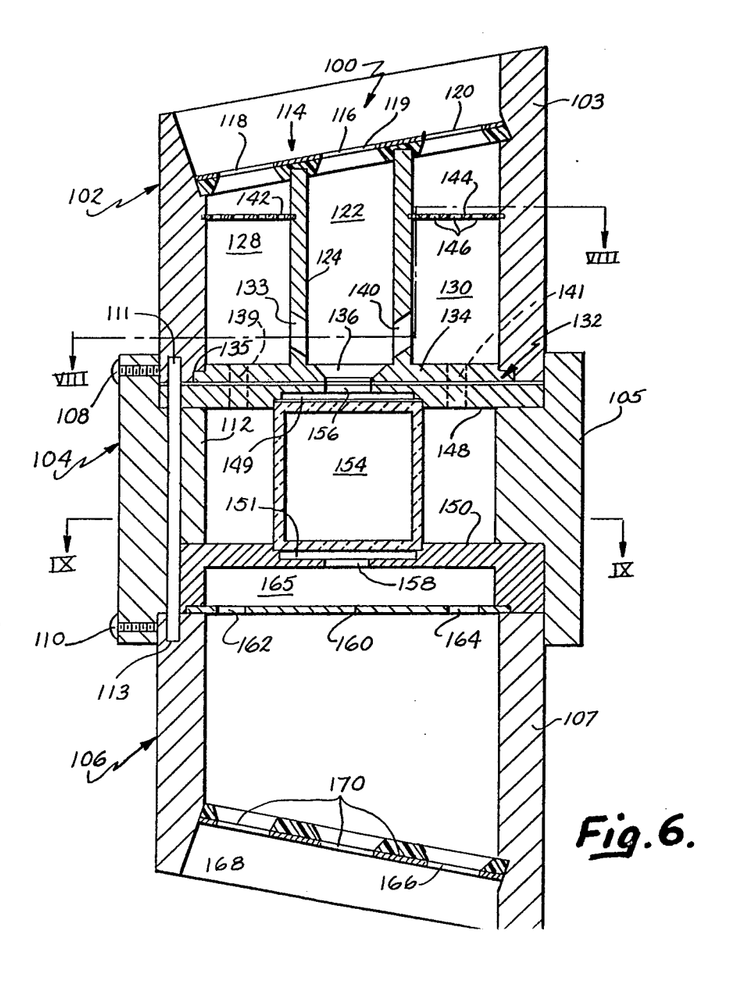
FIG. 6 is a sectional side-elevational view of a second form of calibration instrument in accordance with the invention, taken generally along the compound plane VI—VI of FIG. 4.
Figures 7, 8, 9:
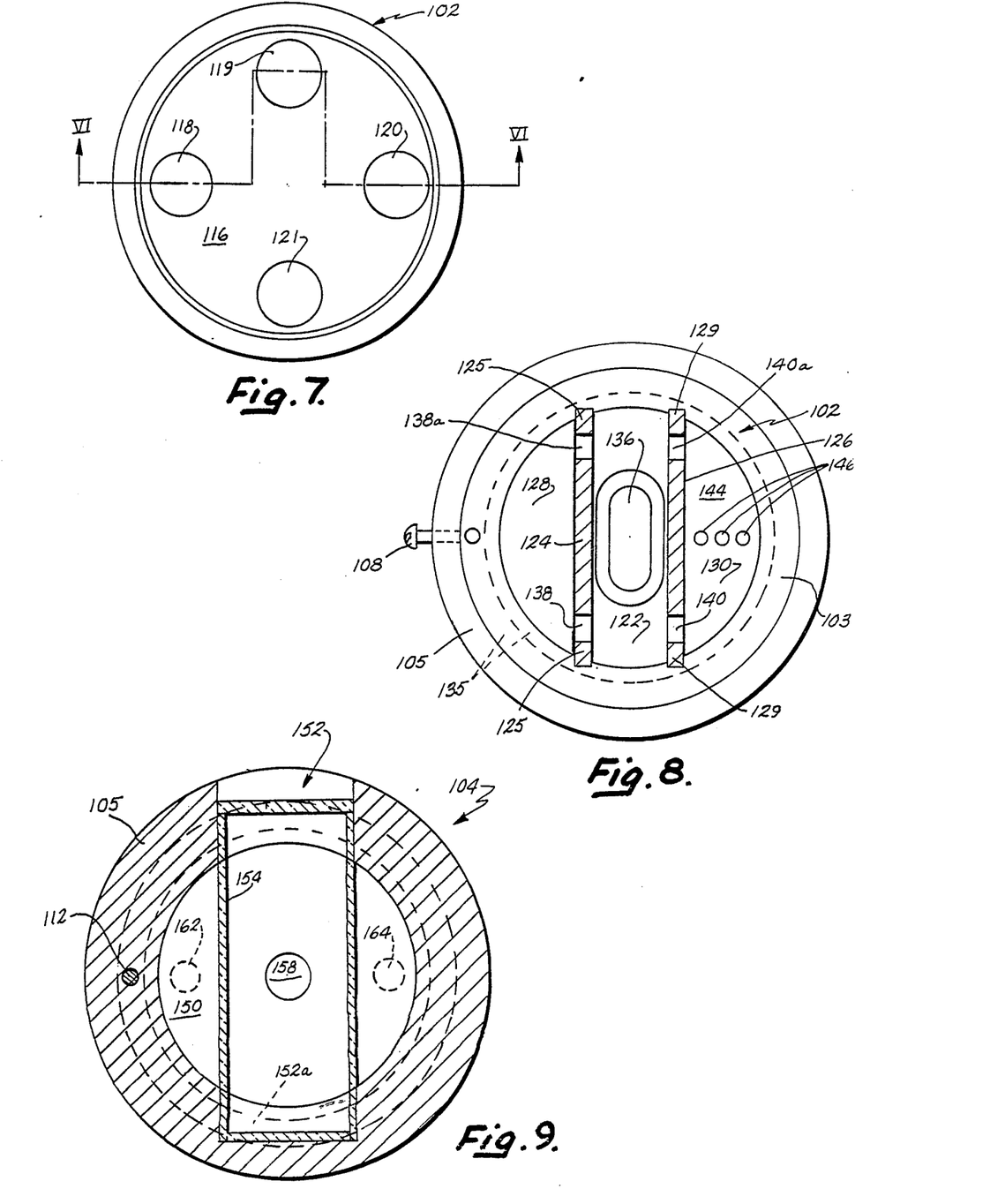
FIG. 7 is an overhead plan view of the apparatus shown in FIG. 6.
FIG. 8 is a sectional plan view taken along the compound plane VIII—VIII of FIG. 6.
FIG. 9 is a sectional plan view taken along the plane IX—IX of FIG. 6.

Accordingly, light from the probe terminal injection sources enters the injector coupling module 102 through openings 119 and 121, and communicating with those openings is a centrally-located diffusion or sample chamber 122 established by parllel septa 124 and 126 which extend as chords across the circular internal cross section of injector module 102, parallel to a diameter thereof (FIGS. 6 and 8). In addition to the central diffusion chamber 122, the septa 124 and 126 thus also define oppositely-spaced lateral diffusion chambers 128 and 130, each of which has one rectilinear side defined by the particular septa involved and one curvilinear (semi-circular) side defined by the adjacent inner sidewall of the tubular housing 103 constituting the outer wall of the injector coupling 102. Chambers 128 and 130 thus are in alignment with the "near" detector apertures 118 and 120, repectively, noted above. The top of all three such diffusion chambers is defined by the aforementioned reflector plate 116 which closes each chamber except to the extent of the apertures 118-120 inclusive, as noted above. A soft, resiliently deformable seal 125 (FIG. 6) seats atop the septa 124 and 126 and extends around the inside edge of the tubular housing 103 in a shoulder provided there, for mounting and seating the reflector plate 116 in place atop injector module 102. The seal 125 also operates to seal the end portions of the optical probe to the injector module, at the same time sealing the periphery of each light-injecting or light-detecting optical cable bundle, light source, or detector in the probe, as the case may be.

The septa 124 and 126 preferably constitute an integral part of a septal insert 132, which includes a circularly-shaped base portion 134 from which the septa 124 and 126 project upwardly. Base portion 134 preferably has a stepped periphery defining a shoulder 135 for closely interfitting with the complementary end extremities of housing 103, to which the septal insert should be releasably secured (in any desired conventional manner). The base portion 134 also defines a generally oval central aperture 136 (FIG. 8) through which part of the injected light may pass, as described more fully below. Further, each of the parallel septa 124, 126 define a pair of spaced angularly-disposed, light-passage apertures 138, 138a, and 140, 140a, respectively near the point where the septa join the circular base 134 (FIGS. 6 and 8), the axis of such apertures preferably being tilted on an angle of about thirty degrees with respect to the plane of the base 134, as discussed more fully hereinafter. The opposite end extremities 125 and 127, respectively (FIG. 8) of the septa 124 and 126 preferably project at least slightly beyond the innermost edge of the shoulder 135 and are received within closely-fitting corresponding recesses formed in the inside wall surfaces of the tubular housing 103.

As seen in FIG. 6, each of the two diffusion chambers 128 and 130 includes an apertured attenuation plate 142, 144, respectively, extending between the tubular outer peripheral wall of housing 103 and the nearest septa 124 or 126 and located toward the top of each such chamber, a short distance below the reflector plate 116. Each such attentuaion plate may be mounted in the desired position by seating in an appropriate slot formed in each of the septa, as indicated, and the circularly-curved outer periphery of the attenuation plates should contact the similarly-curved inner wall surface of the tubular housing 103. Each of the attenuation plates 142, 144 should have a small number (e.g., three) of small apertures 146 (FIGS. 6 and 8), which in a preferred embodiment correlate to the optical response process described in co-pending application Ser. No. 542,022, are on the order of about 0.020 inch in diameter and spaced about 0.050 inch apart.

As already indicated, the injector coupling module 102 seats atop and nests into the top of the calibrator module 104 (FIG. 6). Basically, the latter comprises a tubular housing 105 having centrally-apertured closure plates 148, 150 at each opposite end, which may be permanently secured in position. Preferably, the opposite ends of the tubular housing 105 are annularly recessed in the manner illustrated, so as to provide an annular seat for telescopingly receiving the respective ends of the modules 102 and 106. The respective closure plates 148 and 150 are receivable within such annular recesses, such that the inserted ends of the modules 102 and 106 abut the outer surfaces of the closure plates, with the alignment pin 112 projecting outwardly through each such closure plate, so that its respective ends 111 and 113 are receivable within complementary recesses in the end surfaces of the respective modules 102 and 106.

The inner surface of each of the closure plates 148 and 150 defines a generally rectangular, step-sided recess 149, 151, respectively, (FIGS. 6 and 9). These recesses extend in a first direction toward tubular wall 105 to form a generally rectangular closed (blind) recess 152(a) (FIG. 9), and also extend in the opposite direction outwardly through one side of the closure plates and through the adjacent tubular wall 105 to define the top and bottom of an access opening 152. This opening also includes the entire rectangular area of tubular wall 105 located between recesses 149 and 151; that is, such wall portion is also cut away. Accordingly, access opening 152 actually extends through one side of tubular housing 105 and across the longitudinal axis thereof, along a diameter of the housing and of the top and bottom closure plates 148 and 150.

The cross-sectional shape of access opening 152 is of a size and shape to closely receive a sample cell designated 154 in FIG. 6, which may be a conventional laboratory cuvette. Accordingly, such a sample cell may be inserted into position within the interior of the calibration module 104 by insertion through the access opening 152 in the tubular wall thereof, and may be withdrawn from such position in the opposite manner. While in the inserted position, the sample cell will be disposed in a generally concentric position intersecting the longitudinal axis of the calibration module. Both of the closure plates 148 and 150 have a central, axial aperture, designated 156 and 158, respectively. The upper such aperture 156 is axially aligned with the oval aperture 136 in the injector module 102 when these two modules are fitted together in their nested operating position, illustrated in FIG. 6. Beneath the lower aperture 158 is disposed an exit aperture plate 160, which is secured in place over the circular end opening defined by closure plate 160, as for example by seating within an appropriate annular recess formed in the edge thereof. The exit aperture plate 160 is closed at its center, i.e., in alignment with aperture 158, but it defines a small number (e.g., two) of somewhat smaller exit apertures 162 and 164 which are radially spaced from is center, near its outer periphery (FIGS. 6 and 9).

As previously indicated, the detector module 106 (FIG. 6) is received within the recessed end extremity of the calibrator module 104, contiguous to the exit aperture plate 160 noted just above. Basically, the detector module 106 is similar in many respects to the injector module 102, except for having no septal insert. Instead, detector module 106 basically comprises a tubular housing 107 which is received within the recessed end extremity of calibrator module 104, contiguous to the exit aperture plate 160. Preferably, detector module 106 has an appropriate guide opening formed in the upwardly-facing end extremity of its tubular housing 107, to receive the projecting end extremity 113 of the guide pin 112, and in this manner a desired orientation of the detector module may be obtained analogous to the orientation of injector module 102.

The detector modules 106, while having no septal insert, nonetheless should have a reflector plate 166 at its lower end opening. Reflector plate 166 is analogous to reflector plate 116, at the inlet to the injector module 102, and may be similarly seated upon a soft, resilient elastomeric seal 168 of an annular shape. While similar or analogous to the inlet reflector plate 116, the exit or outlet reflector plate 166 should have an array of outlet apertures 170 whose size, shape, and pattern is representative of the optical probe member or probe terminal with which the detector module is to mate. Generally speaking, such an optical probe may be expected to have the characteristics of the probe terminal 14 illustrated in FIGS. 1 and 3 hereof, although it is to be noted that other arrangements and details for optical probe terminals with which the present invention is equally usable are certainly possible. One such alternate form of probe terminal is shown in the above-noted co-pending application Ser. No. 827,526, which is commonly owned with the present application. The characteristics of such a probe may include optical cable endings used directly as light receptors, rather than the electrically-operative photo-voltaic cells or photo-diodes referred to above in connection with the apparatus of FIG. 3. Of course, the light received by such a direct cable-end receptor will typically be coupled to an electro-optical detector or conversion device at a related equipment console, for signal processing of an electrical nature.

With respect to further sturctural or physical details or aspects of the calibrator 100, it should be noted that all of the interior optical surfaces of all of the modules are preferably finished so as to have one of two possible charcteristics, i.e., either a very efficient diffuse reflective finish (e.g., gold flash, white photographic reflectance coating, the coating known as "Kodak reflecting paint", or else an efficient absorber (e.g., flat carbon black). More particualrly, a diffuse reflecting finish of the aforementioned type should be used on all interior surfaces of the injector module 102 and the detector module 106, except for the surface of the attenuator plates 142 and 144 and the top of the reflector plate 116, both of which should have flat, absorbing black finishes. As previously noted, the optical probe terminals should telescope smoothly and snugly into the tubular end portions of the modules 102 and 106, perpendicular to the apertured plates 116 and 166, with no escape of light, and the apertures in plates 116 and 166 should be at least slightly oversized with respect to the optical cable bundles or other optical components of the probe terminals with which such apertures are to match up for optical transmission, so that all of the light from the optical probe terminal enters the calibration device and none of the light exiting the calibration device is lost to the ambient environment. Preferably, to help accomplish the latter, even the annular sloping interior surfaces of the apertures 118-121, inclusive, should have a highly diffusive, reflective finish. The calibrator module 104 should also typically have all of its inside surfaces between closure plates 148 and 150 finished to provide a diffuse, reflecting surface, and the shoulder recesses 149 and 151 should be closely fitted to the corners of the sample cell 154 so that the latter is held in place essentially by contact with these shoulder areas alone. In this manner, the relatively fragile reflective finishes within the recesses are protected from abrading contact with the flat end surfaces of the sample cell, and will not be worn away by the latter as a result of numerous insertions and withdrawals. Preferably, the upper closure plate 148 is made to be removable from the calibrator module 104, although the lower closure plate 150 may be permanently assembled with respect thereto. The exit aperture plate 160, however, should also be made to be removable, since the size and location of the apertures therein comprise a selectable parameter determined by the nature of the calibration process to be carried out. The outer end surfaces of the lower closure plate 150 and the adjacent interior surfaces of the exit aperture plate 160 should all be finished with a diffuse, reflecting finish of the type noted above, since this area in effect constitutes a secondary chamber immediately adjacent that in which the sample cell 154 is located. This secondary chamber functions as an "integrating sphere", from which emergent light may pass through the exit apertures 162 and 164 into the detector module 106.

The manner of using the calibration o' correlation apparatus in accordance with the invention, and the methodology involved therein, is as follows. Generally speaking, the device 50 or 100 is placed in position between the two optical probe terminals, as described above, with a selected media in the appropriate chamber. The light source (or sources) within either or both of the probe terminals is then activated, preferably in the same manner as occurs during actual operation of the optical instrumentation to obtain data from a subject. For example, the light source may be driven by appropriate illuminators and optical filters to emit a sequence of timed bursts of different selected light spectra. At the same time, the detectors or receivers are monitored to determine the quantity of light energy received at the different receiver positions.

In such operation, light from the source initially entering the device 50 of the first embodiment first encounters the first diffusion chamber 62, which may contain an air media as shown or another substance, as described above. In this chamber, the light rays are initially directed through the media and at the closed bottom surface of the chamber (i.e., interior wall 72 at the bottom fo the insert cup 58). From this surface, the light rays are reflected and widely diffused, a certain proportion thereof passing through the two mutually spaced apertures 68a, 68b near the bottom of septum 60, and entering the second chamber 64. Depending upon the spectrum or band of light involved, the two apertures 68a and 68b should be rather small, e.g., if the light is within the near-infrared band and within the range of from abou 0.6 nm up to about 1.5 nm, apertures 68a and 68b may be on the order of about 0.6 nm.

The second chamber 64 may also contain a selected media other than air, either in addition to or instead of the media contained in chamber 62. In either event, some of the light entering chamber 64 through apertures 68a and 68b will exit that chamber upwardly and be received by the "near" detector or receptor aligned therewith. Other light will exit downwardly, through aperature 70, and enter the third chamber 66. The near-axial aperture 70, which is located generally centrally with respect to the base wall 72 of the insert cup (although slightly off-axis with respect thereto) is preferably on the order of about 2 millimeters in diameter for an application of the type described. It is preferable that both the apertures 68 (i.e., 68a and 68b) and 70 be beveled, or countersunk, on both sides, as illustrated in FIGS. 4 and 5, to facilitate light transfer through them.

It should also be noted in connection with use and operation of the calibrator 50, that the third chamber 66 may be used as the one to contain selected non-air media, particularly if it is desired to have the light received by the "near" receptor subjected to only media other than that to which the light received by the "far" receptor is subjected. In this event, a complementary-shaped sample cell containing the desired media may be inserted into chamber 66 through the recessed end 54 of tubular housing 52 and retained therein in any convenient manner. Of course, a series of different individual calibrators 50 may be prepared with a specific non-changeable media "built in" each, by use of permanently-mounted sample cells or by using transparent seals or diaphragms to cover affected apertures with the walls of the chambers themselves in contact with the contained media. However the media particulars are implemented, a certain amount of the light entering chamber 64 will exit the same downwardly, to be collected by the "far" receptor aligned and communicating therewith.

In view of the foregoing description it will be seen that the calibration apparatus 50 actually incorporates two relatively separate and distinct outlet passages or areas, one being at the open end of diffusion chamber 64 and the other being at the open end of diffusion chamber 66. As will be recognized, this arrangement facilitates the type of probe terminals 12 and 14 illustrated in FIGS. 1-3 inclusive, which incorporates both "near" and "far" light-receivers or detectors, i.e., mutually-independent detectors located at different relative distances from the light-injecting source. In such an arrangement, the "near" receivers are not necessarily located directly adjacent the light source, as illustrated in the preferred embodiments referred to herein, but could also (for example) be located at some further distance from the point of light injection. In this event, the intermediate diffusion chamber 64 would have its outlet positioned differently, although the general arrangement (succession of intercommunicating diffusion chambers) would remain the same. Somewhat similarly, the "far" receivers are not necessarily located within the axial silhouette of the point of light injection, but could be angularlyl disposed with respect thereto, in which event the outlet of chamber 66 would be differently positioned even though the general arrangement would continue to be the same, or analogous.

Generally speaking, the overall operation and use of the calibration device 100 is analogous to that discussed above in connection with the calibrator 50. In the case of the calibrator 100, however, light from the illuminator sources first enters the center chamber 122, in which it is widely scattered and diffused, and ultimately exists through the various apertures 136, 138 and 138a, and/or 140 and 140a. In this respect, the angulation of the last-mentioned four apertures is important since light passing through these apertures and entering the lateral chambers 128 and 130 is ultimately received by the "near" receptors which communicate with these chambers through apertures 118 and 120 in the reflector plate 116. Consequently, it is important that these receptors receive only diffused and reflected (scattered) light rather than any light rays directly passing from the injection source through the central chamber 122 and into the lateral chambers 128, 130. The location and spacing of the apertures 138 and 140 with respect to the central aperture 136 also facilitates this end, as does the sloping or beveled sides of aperture 136 which, in addition to channeling down the actual size of this aperture, also serve to reflect impinging light rays back in the general direction of the angled aperture 138 and 140. The attenuation plates 142 and 146 further serve to reflect and diffuse the light present in lateral chambers 128 and 130 before it reaches the "near" receptors, and of course attenuate the amount of light received by the latter.

With further reference to the use in operation of the calibrator 100, the injected light which does pass through central chamber 122 and through its outlet aperture 136 immediately encounters and passes through aperture 156 in the top of calibrator module 104, directly beneath which is the sample cell 154. Basically, this sample cell may be considered to be a transparent envelope (container) which is filled with one of the media referred to above, or other such media selected for other reasons. According to a preferred mode of calibration or correlation, a pair of such sample cells is used, the first of which contains water and the second of which contains carbon tetrachloride or an optical equivalent, e.g., fused quartz.

The incipient light applied to the sample cell 154 transmisses the latter as a function of the absorption characteristics of its contents, the light rays which do pass completely through the sample cell and media exiting the calibration module 104 through its exit aperture 158. From this point, the exiting light is reflected once again off the central portion of the exit aperture plate 160, is scattered and diffused within the "integrating sphere" area 165 above plate 160, and then leaves that area through its exit apertures 162 and 164. Following this, the emergent light rays pass outwardly through whichever of the apertures 170 in bottom reflector plate 166 as are in the appropriate location and, following their passage through such reflector plate apertures these light rays are ultimately received by the particular receptors which are positioned in close registration with their corresponding outlet apertures.

It should be noted here it is also within the concepts of the invention to provide at least a selected portion of the light which is reflected and scattered back to the "near" receptors (through chambers 128 and 130 and through reflector plate apertures 118 and 120) as a function of the transmissivity of the media in the sample cell 154. This may be accomplished by providing additional (or alternative) apertures 139 and 141 (FIG. 6) upwardly through closure plate 148 and septal wall 134, and by downsizing (or closing) the apertures 138, 138a and 140, 140a as required. Also, at least an upper portion of the tubular wall 105 and the underside of closure plate 148 are then finished with the aforementioned highly-diffusive coating. An alternative approach is to locate a sample cell or other media supply in the upper chambers, for example in central chamber 122 or in lateral chambers 128 and 130.

The basic purpose underlying use of the calibration apparatus disclosed in accordance herewith, as will by now be appreciated, is to provide a way to ascertain whether, and/or a basis for ensuring that, the optical-response data provided by a given optical probe instrument (i.e., in a most preferred, and most typical, case a complete unit of optical response equipment) is effectively the same as optical-response data obtained from the same unit of equipment at an earlier point in time, as well as being effectively the same as the results which could be obtained from any or all other ostensibly identical units of such optical-response instrumentation. In accomplishing this goal, the calibration apparatus provided herewith initially serves to isolate the optical instrument being calibrated from extraneous influences, while at the same time providing consistent, uniform and known attentuation and diffusion characteristics suited to testing system sensitivity, repeatability, etc. Of course, the required degree of sameness in the results obtained from different units of optical-response equipment, or even from the same unit at a different point in time, is largely a function of the particular investigation purposes for which the equipment is to be used, and in a general sense it may or may not be necessary that the optical instruments provide virtually indentical results at all times. To the extent that unacceptable differences are found to exist, there may be a number of particular ways available in which suitable corrective measures can be taken. That is, while it might be thought that the most apparent such recourse would be to make suitable alteration or adjustment of the optical instruments being calibrated, other appropriate (and preferred) procedures would include, for example, applying an appropriate bias or scale factor (e.g., system gain or transfer function) to the data produced by the light-detectors prior to or during processing of such data prior to outputting it; for example, various arithmetic scale factors or computation routines may readily be implemented (particularly by microprocessor) to accomplish this purpose automatically in the preparation of the ultimate output information, such as interpretive charts, tables, plots, etc. Such scale or correction factors, once determined by use of the present calibration apparatus, should thus be stored in computer memory and could be updated at any time, and from time to time, as often as necesary, to insure that the information actually obtained by operating the optical-response instrumentation continues on an acceptably accurate and consistent basis each time the same is used and throughout the operational lifetime thereof, thus providing the highly desirable attribute of uniformity and consistency in the data obtained, enabling meaningful comparison, averaging, etc., of all such data even though obtained by different units of equipment and/or at different points in time.

. In a more definitive sense, the present invention provides for considerably more calibration (or correlation) effects than those noted above, and in fact provides for new and novel concepts and methodologies in the use of the optical testing equipment itself to obtain meaningful data from actual subjects. In a sense, the invention thus provides both methods and apparatus for modeling a "laboratory standard" specimen for evaluation by optical-resposne equipment, even to the extent of simulating in vivo tissue characteristics. Methodolgies involving utilization of such standardized optical response specimens may, and preferably do, constitute steps and procedures which are integrally involved in the actual utilization of the optical probe and test equipment itself in obtaining optical response data from the actual specimens desired to be evaluated, in particular, from living humans.

More particularly, and with reference to use of the same basic types of optical response equipment and methodologies set forth in the above-references (and incorporated) co-pending applications (Ser. No. 542,022, it should be noted that the optical response data to which reference is made is based upon the detected amounts of various light spectra received at "near" and "far" receptors placed in proximity to a given particular tissue subject which is to be evaluated, e.g., in a particular case the living tissue in human female breast anatomy, following "injection" of such light spectra at some location on the breast or other tissue subject or specimen. The detected light energy magnitudes are thus inherently a function of such variables as the particular level of injected light, the nature of the tissue through which the light passes prior to its detection and the length of the optical path involved, degradation or change in detector response and performance and/or in detector circuit response and performance (circuit gains and parameter shifts, etc.), and the like. In such circumstances, assuming the absence of any significant amount of light loss by escape or the like, all such factors will likely be accurately repeatable from one cycle of equipment operation to the next successive cycle, run at essentially the same point in time, except for the extent to which the characteristics of the tissue under examination actually do change. As to this, the factor of greatest influence in the optical response of different tissue subjects or specimens involves the presence of water in the tissue, and the particularities with which such water is present, due to the known absorption peaks or bands in water when considered as a light-transmission media. In accordance with the present invention, a standard tissue subject or specimen is in effect provided, by conducting two successive cycles of operation of the optical response equipment, one being with a water media in the calibration apparatus and the other being with a different and preferably "transparent" media which does not have the characteristic absorption bands exhibited by water, e.g., carbon tetrachloride, fused quartz, etc.

While it is eminently useful to merely conduct the two successive calibration cycles with the two different types of media as noted above (e.g., water and carbon tetrachloride) and produce resultant response data for conducting correlation and comparisons with comparable optical-response data taken at other points of time and/or with other specific examples or units of optical response equipment, even more meaningful results are provided in accordance with further aspects of the present invention by ratioing or otherwise representatively combining the results of the two different calibration cycles or scans, particularly for each different light wavelength or spectra utilized in a scan spectrum constituting a number of such spectra sequenced one after the next. In this manner, the results produced by such ratioing (or other representative treatment) have in effect had deleted from them all system parameters which may be variable or subject to degradation, such as gains, attenuation factors, etc., leaving only the then-current actual response value at each such spectra. As will be apparent, the actual obtaining of the ratio or scale rseults just described may readily be accomplished in an automatic and instantaneous manner as the light spectra are scanned, under microprocessor control and by simple microprocessor arithmetic routine, the first set of values obtained with one media being stored in memory and ratioed or scaled against the next ensuing set of values obtained with a different media, on a correlated and coordinated basis. The results of such ratioing or scaling are then stored in memory as an available table, e.g., a table of scale factors, or a conversion table.

Accordingly, a stored table of the type just described may be used for any desired length of time, and may be updated at any time by simply running two new successive scans, one for each of the different calibration media. This may be done under program control, and the resulting new conversion table may be utilized in each successive actual operation of the optical equipment in obtaining data from different subjects, including living human subjects. That is, the actual detector output values obtained in subsequent scans of living subjects may be modified (i.e., corrected) prior to actual use in analysis or the like by applying the stored conversion or scale factors obtained for each different light spectra, thereby in effect converting the actual values obtained from the detectors into corrected response data which is fully harmonious with (correlated with) all response data take2n from other subjects at other points in time, as well as with all of the other response data taken by other optical instrumentation which has been similarly "initialized" by having updated conversion or scale tables stored by running successive scans with calibration apparatus in accordance herewith.

It should be clearly understood that the foregoing procedure and methodology constitutes a fundamental and singularly important step in achieving the fully correlated response data which is essential in having consistent and reliable use of optical response equipment for diagnostic or evaluation purposes, of the type described and incorporated herein by reference. Once again, while the results (values) obtained in conducting the calibration scans are useful in various ways to condition the test equipment so that the detector outputs themselves are regulated, harmonious, and repeatable at all times, the preferred approach is to use the ratio-based data-conversion scale factor techniques described above, since this may readily be accomplished through the agency of computer capabilities, and also since the procedure is actually a direct way in which to obtain final outputs (as by plots, graphs, etc.) based upon values which are themselves compatible with all other such values taken from other equipment, etc.

It remains to be stated that the apparatus disclosed herein also lends itself to an additional or alternative usage constituting additional important subject matter and methodology useful in the ultimate practice of optical-response testing and evaluation. That is, in addition to providing a convenient way in which to evaluate and condition the basic response operation of the optical equipment by use of selected media contained within the sample cells 154 (and in the other ways referred to above), the sample cells 154 may also be utilized as a container for actual tissue samples or specimens for which optical response data is desired to be obtained. By way of general illustration, viable tissue samples obtained during surgical procedures such as biopsy and the like may be placed within a sample cell 154 and the latter positioned in the calibration apparatus as shown in FIG. 6, following which the optical response apparatus may be run through a typical (or other) operating cycle. In this manner, optical-response data may actually be obtained from excised tissue as well as from living tissue examined in situ, as noted above. Such optical-response data is not collected for purposes of calibration or correlation with other response data, or for system output conversion, as in the case of the calibration procedures referred to above, but is typically useful in and of itself, as indicative of conditions or characteristics of the examined tissue sample and of the individual from which the same was obtained.

It is to be understood that the above is merely a description of a preferred embodiment of the invention and that various changes, alterations and variations may be made without departing from the underlying concepts and broader aspects of the invention as set forth in the appended claims, which are to be interpreted in accordance with the established principles of patent law, including the doctrine of equivalents.

The embodiments of the invention in which an exclusive property or privilege is claimed are defined as follows:

1. Apparatus for calibrating optical-response in-vivo tissue-examination apparatus of the type having an optical probe with at least one light-sending terminal portion adapted for introducing examination light into a living mammalian subject and a terminal portion for receiving resulting light from said mammalian subject, said apparatus comprising: a body having outer walls defining and enclosing areas of internal space, said body having at least one inlet aperture and at least one outlet aperture; means communicating with at least one of said inlet and one of said outlet apertures for cooperatively receiving said light-sending and said light-receiving terminal portions of said optical probe, in a manner substantially precluding entry and exit of ambient light; and means within said body for guiding light energy admitted into said body at said inlet, including means for conveying at least certain of such light energy along at least one defined tortuous path through at least certain of said body spaces and communicating with said outlet aperture.

2. Optical probe calibration apparatus according to claim 1, and including means within said body defining at least one restricted aperture having an axis disposed at an angle with respect to the longitudinal axis of said body.

3. Optical probe calibration apparatus according to claim 1, and including a first diffusion chamber within said body adjacent to and communicating with said inlet aperture, and further including means defining at least one restricted aperture within said diffusion chamber for passing light out of said chamber which was admitted through said inlet aperture.

4. Optical probe calibration apparatus according to claim 3, and including means defining at least one additional diffusion chamber located adjacent said first diffusion chamber and in light-communication therewith.

5. Optical probe calibration apparatus according to claim 4, and including means defining at least one light-transmission path communicating through said additional diffusion chamber and in communication with a first outlet aperture of said body.

6. Optical probe calibration apparatus according to claim 5, wherein said first outlet aperture of said body is located generally adjacent said inlet aperture.

7. Optical probe calibration apparatus according to claim 6, and including at least one restricted aperture providing a light-conducting passage exiting from at least one of said diffusion chambers at a point remote from said first outlet aperture.

8. Optical probe calibration apparatus according to claim 7, and including means defining a second outlet aperture for passing light out of said body, said second outlet aperture being in light-communicating relation with said restricted aperture and providing a light-conducting passage which exits at a point remote from said first outlet aperture.

9. Optical probe calibration apparatus according to claim 8, and including at least one other diffusion chamber disposed between and in light-communicating relation with both said restricted aperture exiting from said additional diffusion chamber at a point remote from said first outlet aperture and said second outlet aperture.

10. Optical probe calibration apparatus according to claim 1, and including a chamber within said body for containing selected media, said chamber being disposed along and in light-intercepting relation with said light-transmission path.

11. Optical probe calibration apparatus according to claim 10, wherein said media-containing chamber comprises a removable receptacle, and including means defining an access opening in said body affording access to said receptacle while therewithin.

12. Optical probe calibration apparatus according to claim 11, wherein said receptacle is selectively removable from and reinsertable into said body by way of said access opening.

13. Optical probe calibration apparatus according to claim 12, and including a medium within said receptacle which has light-transmission characteristics similar to those for water.

14. Optical probe calibration apparatus according to claim 13, and including a second and different medium within said receptacle having light-transmission charcteristics different than those for water.

15. Optical probe calibration apparatus according to claim 14, wherein said second and different medium has light-transmission characteristics similar to those of carbon tetrachloride.

16. A wide-band attenuator and diffuser apparatus for use as a calibration interface between the sending and receiving terminal portions of an optical probe in an optical-response data-gathering apparatus, comprising: a generally tubular body having substantially opaque walls; said body having at least one light-admitting inlet and at least one light-exiting outlet; and internal baffle wall means inside said body defining a labryinthine light-transmission path extending between said inlet and said outlet, said baffle wall means including a reflection wall within said body having at least a portion extending generally traversely across the extended axis of said inlet to reflect at least certain of the light rays entering said body back along the axis of said inlet and light-guiding wall means connected to said reflection wall and extending generally perpendicular thereto and along said extended axis.

17. The apparatus of claim 16, wherein said inlet and outlet are located at opposite end portions of said body.

18. The apparatus of claim 17, and including a secondary outlet located generally adjacent said inlet.

19. The apparatus of claim 16, and including a receptacle containing a predetermined medium other than air disposed at least partially within said body and at least partially across said light-transmission path such that at least certain of the light exiting said body passes through said receptacle and the medium therewithin.

20. The apparatus of claim 19, wherein said receptacle is removable from the reinsertable into said body to provide for use of different media.

21. The apparatus of claim 20, wherein said receptacle comprises a sample cell adapted to removably receive various selected media.

* * * * *

UNITED STATES PATENT AND TRADEMARK OFFICE
CERTIFICATE OF CORRECTION

PATENT NO. : 4,725,147

DATED : February 16, 1988

INVENTOR(S) : Hugh F. Stoddart

It is certified that error appears in the above-identified patent and that said Letters Patent is hereby corrected as shown below:

Column 3, Line 11;
   "agumenting" should be -- augmenting --.

Column 4, Line 39;
   "he" should be -- the --.

Column 4, Line 47;
   after "aperture" insert -- plate --.

Column 5, Line 33;
   "are" should be -- area --.

Column 6, Lines 54 and 55;
   "apparatus 60" should be -- apparatus 50 --.

Column 6, Line 57;
   "device 60" should be -- device 50 --.

UNITED STATES PATENT AND TRADEMARK OFFICE
CERTIFICATE OF CORRECTION

PATENT NO. : 4,725,147

DATED : February 16, 1988

INVENTOR(S) : Hugh F. Stoddart

It is certified that error appears in the above-identified patent and that said Letters Patent is hereby corrected as shown below:

Column 8, Line 3;
   "parllel" should be -- parallel --.

Column 8, Line 59;
   "attentuaion" should be -- attenuation --.

Column 9, Line 56;
   "closure plate 160" should be -- closure plate 150 --.

Column 9, Line 61;
   "is" should be -- its --.

Column 10, Line 39;
   "sturctural" should be -- structural --.

Column 10, Line 47;
   "particualrly" should be -- particularly --.

UNITED STATES PATENT AND TRADEMARK OFFICE
CERTIFICATE OF CORRECTION

PATENT NO. : 4,725,147
DATED : February 16, 1988
INVENTOR(S) : Hugh F. Stoddart

It is certified that error appears in the above-identified patent and that said Letters Patent is hereby corrected as shown below:

Column 10, Line 50;
 "surface" should be -- surfaces --.

Column 11, Line 51;
 "fo" should be -- of --.

Column 12, Line 52;
 "angularly1" should be -- angularly --.

Column 12, Line 61;
 "exists" should be -- exits --.

Column 13, Line 48;
 after "here" insert -- that --.

Column 14, Line 7;
 "could" should be -- would --.

UNITED STATES PATENT AND TRADEMARK OFFICE
CERTIFICATE OF CORRECTION

PATENT NO. : 4,725,147

DATED : February 16, 1988

INVENTOR(S) : Hugh F. Stoddart

It is certified that error appears in the above-identified patent and that said Letters Patent is hereby corrected as shown below:

Column 14, Lines 63 and 64;
   "speciments" should be -- specimens --.

Column 15, Line 63;
   "rseults" should be -- results --.

Column 16, Line 22;
   "take2n" should be -- taken --.

Column 18, Claim 14, Lines 28 and 29;
   "charcteristics" should be -- characteristics --.

Signed and Sealed this

Eleventh Day of October, 1988

*Attest:*

DONALD J. QUIGG

*Attesting Officer*     *Commissioner of Patents and Trademarks*